(12) United States Patent
Sheehan et al.

(10) Patent No.: US 6,319,199 B1
(45) Date of Patent: Nov. 20, 2001

(54) PORTABLE DATA COLLECTION DEVICE

(76) Inventors: David M. Sheehan, 17515 Valley Verde Rd., Poway, CA (US) 92064; Mark J. Nitzberg, 45-A Fayerweather St., Cambridge, MA (US) 02138; Patrick J. Fitzgerald, 12604 Parish Rd., San Diego, CA (US) 92128

( * ) Notice: Subject to any disclaimer, the term of this patent is extended or adjusted under 35 U.S.C. 154(b) by 0 days.

(21) Appl. No.: 09/425,499

(22) Filed: Oct. 22, 1999

Related U.S. Application Data

(60) Provisional application No. 60/105,696, filed on Oct. 26, 1998.
(51) Int. Cl.[7] .................................................. A61B 1/227
(52) U.S. Cl. ............................................ 600/200; 600/184
(58) Field of Search .................................. 600/184, 200, 600/199, 300

(56) References Cited

U.S. PATENT DOCUMENTS

| | | | |
|---|---|---|---|
| 5,239,984 | * | 8/1993 | Cane et al. . |
| 5,527,261 | * | 6/1996 | Monroe et al. ...................... 600/109 |
| 5,701,904 | * | 12/1997 | Simmons et al. ..................... 128/670 |
| 5,762,605 | * | 6/1998 | Cane et al. ........................... 600/200 |
| 5,847,832 | * | 12/1998 | Liskow et al. ....................... 356/376 |
| 5,885,214 | * | 3/1999 | Monroe et al. ...................... 600/407 |
| 6,014,432 | * | 1/2000 | Modney .......................... 379/106.02 |
| 6,032,678 | * | 3/2000 | Rottem ................................. 128/920 |
| 6,106,457 | * | 8/2000 | Perkins et al. .................. 600/200 X |

* cited by examiner

*Primary Examiner*—Jeffrey A. Smith
(74) *Attorney, Agent, or Firm*—Lahive & Cockfield, LLP

(57) ABSTRACT

A portable data collection device is provided for diagnostic image and data collection at a remote location. The device is implemented as an otoscope including a speculum and light source for illumination of the ear canal. A digital camera element collects the reflected images and provides the images to a processor. The processor processes the images using pattern matching techniques and displays and/or stores suitable images. The images are transferred to a base station for subsequent transmission to a remote server or computer, where an authorized party may access and examine the images. An authorization or prescription from the remote server or computer may be required to enable data collection and transmission by the otoscope.

11 Claims, 7 Drawing Sheets

PORTABLE DATA COLLECTION DEVICE

RELATED APPLICATIONS

This application claims the benefit of U.S. Provisional Application No. 60/105,696, filed on Oct. 26, 1998.

FIELD OF THE INVENTION

The present invention relates generally to a portable data collection device and, more particularly, relates to a portable digital otoscopic camera for capturing, processing, displaying, storing and/or exporting images of a subject eardrum.

BACKGROUND AND SUMMARY OF THE INVENTION

Broadly speaking, the present invention provides a data collection device for remote collection of diagnostic and/or image data. The device includes a memory and processor for storing and processing the collected data; a user interface to permit user interaction with the device; and a communication port for exchange of data with an external computer or server. The device is used by an appropriate party, typically a patient, to collect diagnostic and/or image data for later examination. Hence, a patient can collect data at a leisurely pace and in familiar, comfortable surroundings. Preferably, the device is implemented as a handheld otoscope with a self-contained digital camera.

In one embodiment of the present invention, a remote data collection device is in communication with a central server. The data collection device comprises an image sensor for capturing diagnostic images, and a processor for processing the captured images. The device further comprises a memory for storing the captured images, a communications port for transmitting the captured images to the central server and for receiving instructions from the central server, and a user interface to facilitate use of the data collection device by a remote party.

In another embodiment of the present invention, a system for remote data collection is provided. The system comprises a remote, portable otoscope having a controllable light source for illuminating a target area of an ear canal and generating reflected images. A digital camera element captures the reflected images for processing and storage in a memory. A first communications port is provided for transmitting the processed images and receiving instructions. The system also comprises a base unit having a second communications port for receiving images from the otoscope and for transmitting instructions to the otoscope. A central server is in communication with the base unit and receiving images from the base unit and transmits instructions to the base unit. An authorized, prescribing party provides authorizations and prescriptions to the server.

BRIEF DESCRIPTION OF THE DRAWINGS

The present invention is described with reference to the accompanying drawings. In the drawings, like reference numbers indicate identical or functionally similar elements.

DETAILED DESCRIPTION OF PREFERRED EMBODIMENTS

1. Example Environment

Before describing the data collection device of the present invention in detail, an example environment within which the data collection device may operate will be described. One such environment is a prescription-controlled data collection system as disclosed in U.S. patent application Ser. No. 09/426,118, filed on even date herewith and claiming the benefit of U.S. provisional application No. 60/105,692.

Figure 1:
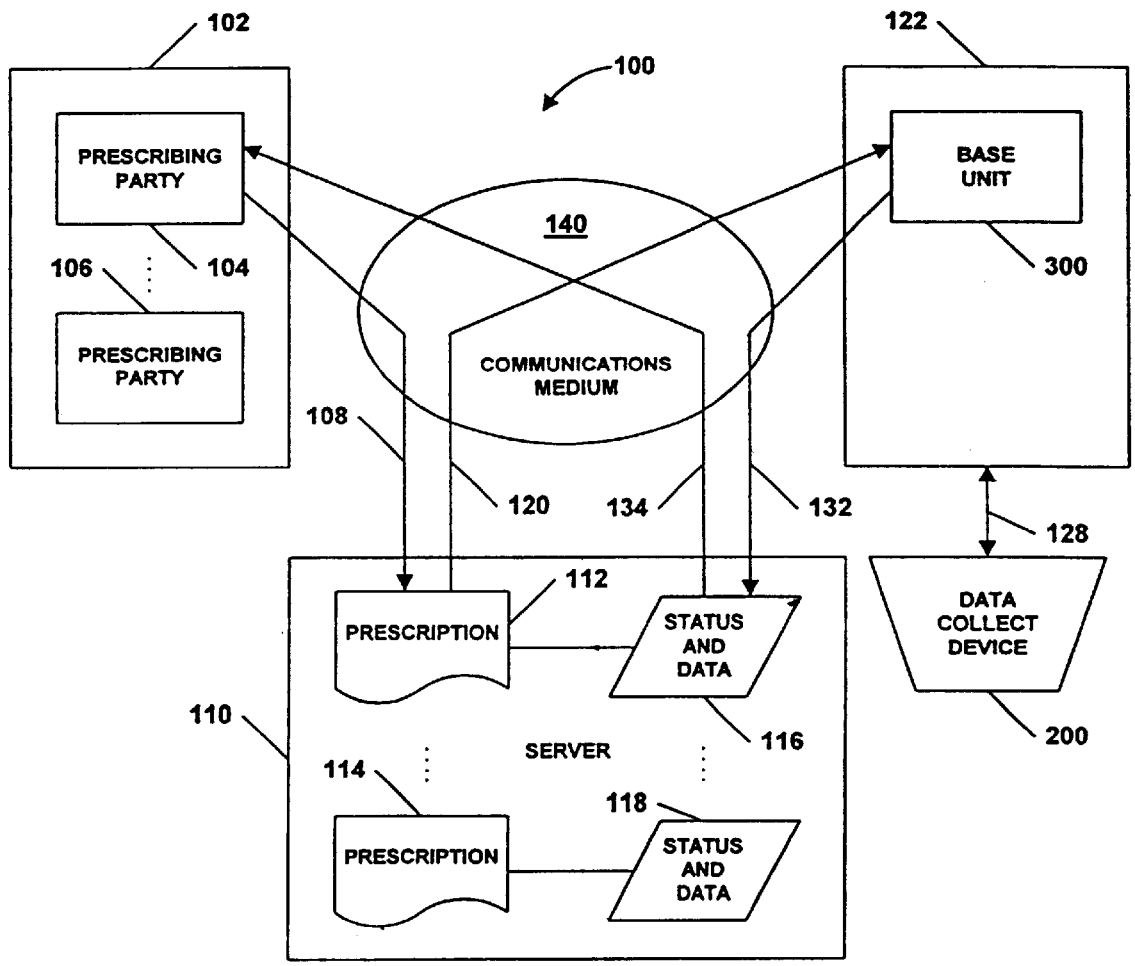
FIG. 1 is a diagram of one sample environment within which a data collection device according to the present invention may be used.

A prescription controlled data collection system 100 is illustrated in FIG. 1. System 100 is just one environment that the data collection device of the present invention may be deployed in; the device of the present invention could also be utilized within alternative environments. System 100 comprises a prescribing party 104, a communications medium 140, a server 110 and a collecting party 122 having a base unit 300 and a data collection device 200. Device 200 and base unit 300 are the subjects of the present application and will be described in more detail below.

In overview, prescribing party 104 writes a prescription 112 that authorizes a collecting party 122 to collect data (line 128) and transfer the data to a central server 110. The status of the prescription and data collected (block 116) are available to a prescribing party 104 having access to server 110. The prescription, authorization, status and data information (indicated by lines 108, 120, 132 and 134 respectively) is exchanged via any suitable data communications medium 140. Medium 140 may comprise any suitable data communications medium including, but not limited to, a wired network, a wireless RF network, a fiber optic network, telephone lines, the Internet or combinations of these mediums.

System 100 improves the efficiency of medical diagnosis and follow-up by allowing a patient to perform diagnostic and follow-up data collection at a remote location. In this example, prescribing party 104 is a doctor or other health service provider having access to central server 110. As indicated by block 102, a plurality of prescribing parties (doctors) 104 . . . 106 may have access to server 110.

Server 110 may be a computer connected to one or more communications media, such as communication medium 140. Server 110 includes appropriate software that allows transfer of data to and from server 110 from remotely located devices and display terminals. Additionally, server 110 will include appropriate software for handling the protocols for prescribing the use of various remote diagnostic devices and for displaying the status of prescriptions and prescription data. In one implementation, server 110 may be a "web server" with associated standard communications protocols for communicating over the Internet.

A doctor 104 having access to server 110 prescribes a particular diagnostic procedure to a patient (collecting party) 122 in a remote location by communicating a prescription (indicated by line 108) to a central server 110 over a communications medium 140. In one example, the prescription authorizes the use of an appropriate diagnostic or data collection device 200 that is in the possession of patient 122.

The prescription process may include registration of device 200 (whose use by the patient is authorized) with server 110. Registration of device 200 is the process by which server 110 associates device 200 with the doctor or prescribing party 104. In one example, a unique device ID number or code identifies device 200 to server 110. This number may be communicated by the prescribing party to the server or, alternatively, assigned by the server to the device. The doctor/device association may be created in server 110 in any suitable fashion. In an example where communication medium 140 is the Internet, doctor 104 may effect registration of device 200 by completing a web form that is transmitted via the Internet to server 110. In another example where medium 140 takes the form of a telephone network, doctor 104 may effect registration of device 200 by calling a telephone service that prompts the doctor to press appropriate touch-tone buttons on a telephone. In a further example, doctor 104 may effect registration by calling or visiting a service whose personnel have access to server 110.

In addition to registration of device 200, the prescription process may also include identification of the doctor 104 to server 110 and identification of the specific data to be collected by the patient. Again, this may be accomplished through use of a web page, a telephone service, or through any other appropriate means. Server 110 may assign each prescription a unique prescription ID number or code. This number will be stored on server 110 (described below), and may also be provided to the prescribing party for future reference.

A particular type or level of authorization may also designate a prescription. In one example, there are two types of prescriptions: a device use prescription and a data transfer prescription. A device use prescription requires device 200 to receive prescription 112 from server 110 before it can function to collect data (line 128) for the prescription. A data transfer prescription, conversely, authorizes transfer of data (line 128) from device 200 to server 110. Hence, once device 200 has been used to collect data (with or without a device use prescription), transfer of the collected data will be blocked unless server 110 has stored a data transfer prescription associated with device 200.

As indicated in FIG. 1, a plurality of prescriptions 112 . . . 114 may be stored on server 110. Server 110 may store a variety of information in connection with each prescription. As described above, server 110 will typically assign a prescription ID number or code to each prescription. Where prescription types are used, the prescription type (i.e. device use, data transfer, or other type) will also be noted and stored. The identity (name) of the prescribing party (doctor, health service provider, or other authorized personnel) will typically be stored, as will the name of the patient associated with the prescription. Incident information, such as the health condition prompting the prescription (i.e., "Tim's right eardrum" or "Ellen's heart monitor") may also be stored. Finally, the prescription will include the date of the prescription; and the expiration date (if any) of the prescription. The expiration date of the prescription is the date after which the prescription no longer authorizes the use of device 200 or the transfer of data.

As is also indicated in FIG. 1, server 110 may store status and data information 116 . . . 118 associated with each prescription 112 . . . 114. The status information may be information such as whether device 200 has been activated (yes/no), or whether data has been transferred (yes/no). The data is the information collected by device 200. Examples include, but are not limited to, otoscopic images, heart monitor signals, breathing rhythm data, and so on.

At some time before or after prescribing party 104 communicates prescription 112 to server 110, the patient (collecting party 122) receives an appropriate diagnostic or data collection device 200 and base unit 300 and is instructed in their use. One suitable device, which is the subject of the present invention, is a digital otoscope and will be described in detail below. Other devices that may be adapted in accordance with the present invention to operate within system 100 include (but are not limited to) rhinoscopes, laryngoscopes, ophthalmoscopes, cameras for dermatology, heart monitors, blood pressure monitors, oxygen saturation monitors, and audio monitors.

It should be noted that there are many industries and environments amenable to use of the data collection device described herein. The prescription-controlled data collection environment discussed above is exemplary only and does not limit the subject invention in any way.

2. Preferred Embodiments of a Data Collection Device

Figure 2:
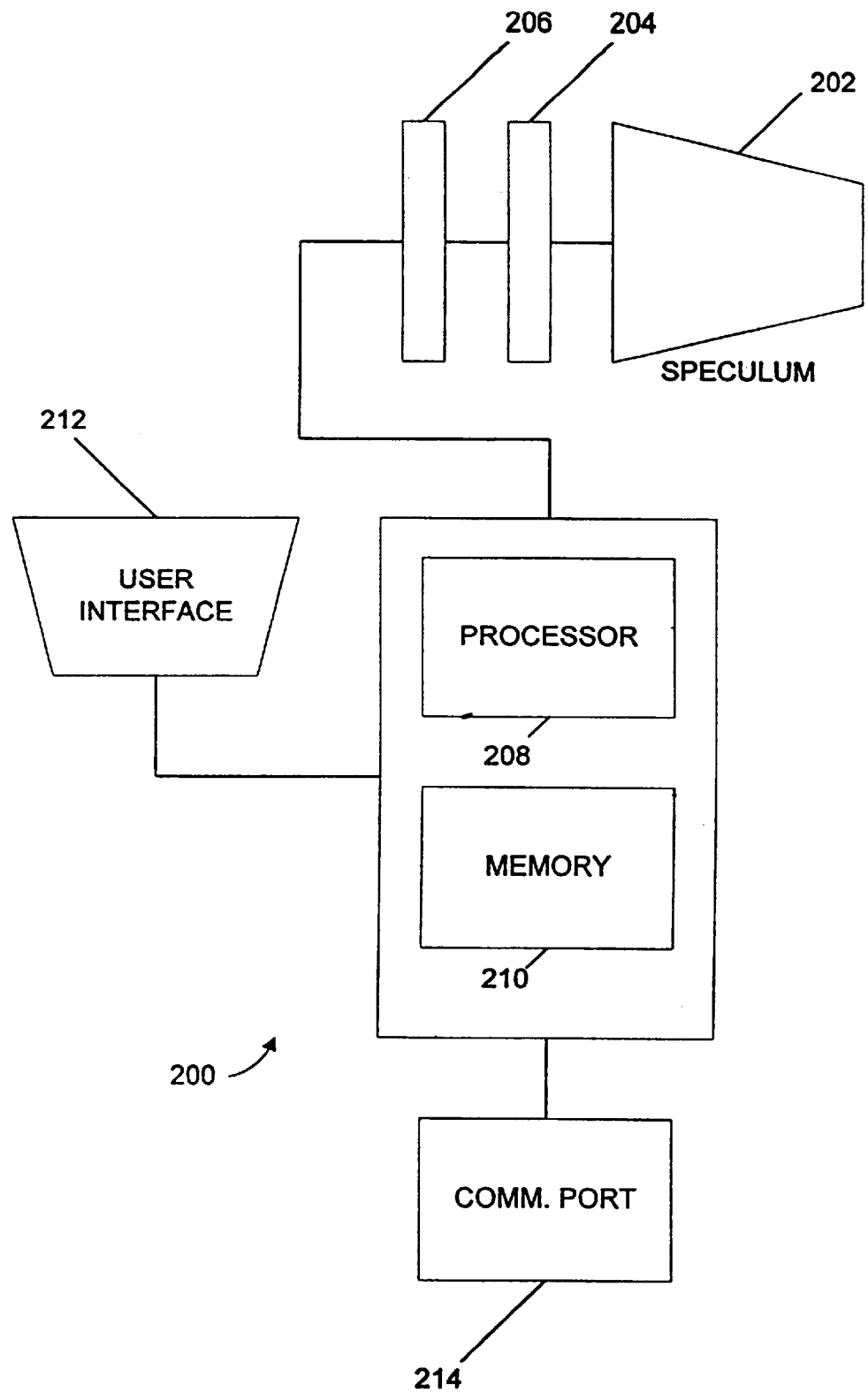
FIG. 2 is a block diagram of a data collection device according to the present invention.
Figure 3:
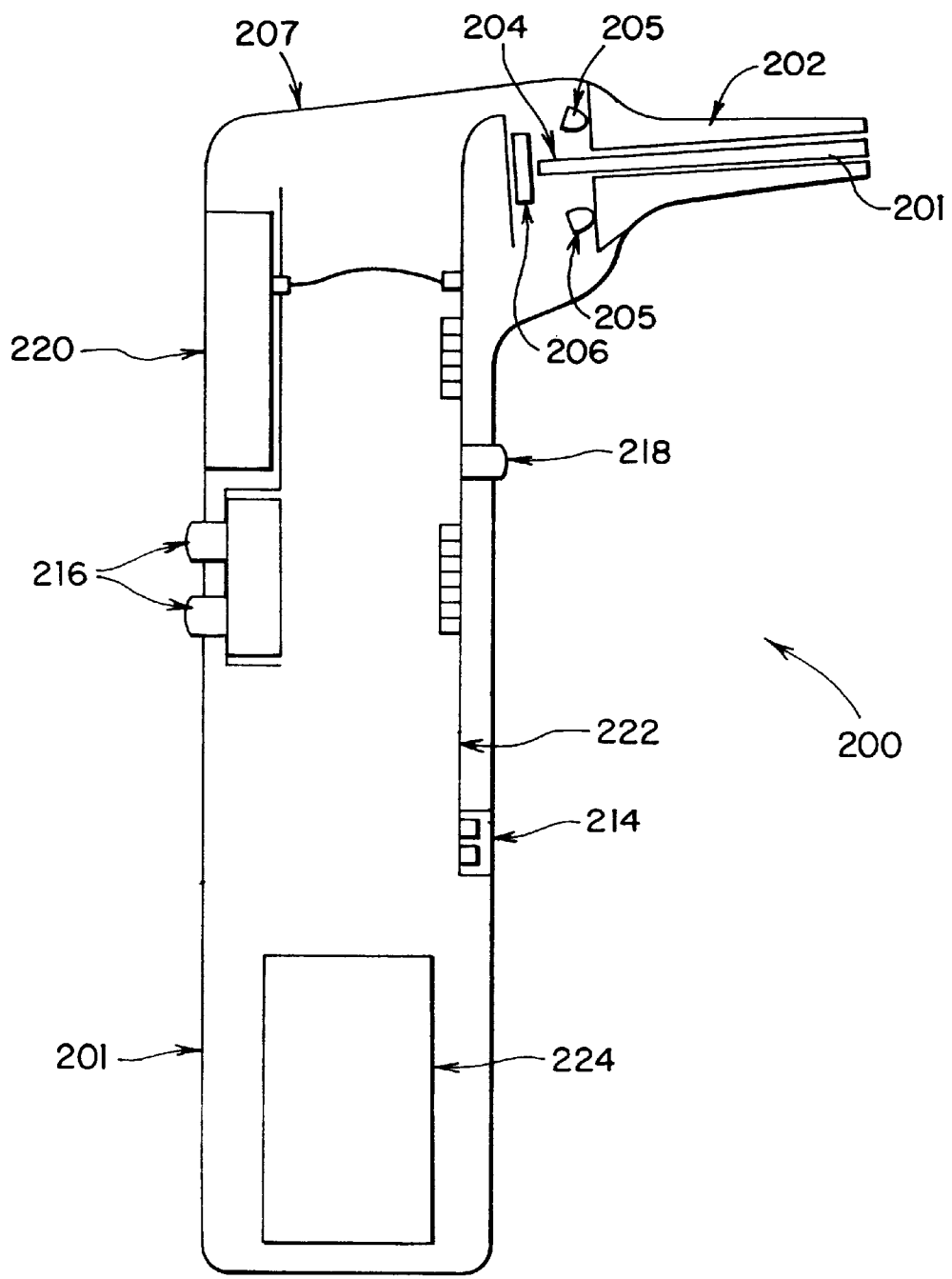
FIG. 3 is a partial sectional view of a handheld otoscope according to the present invention.
Figure 5:
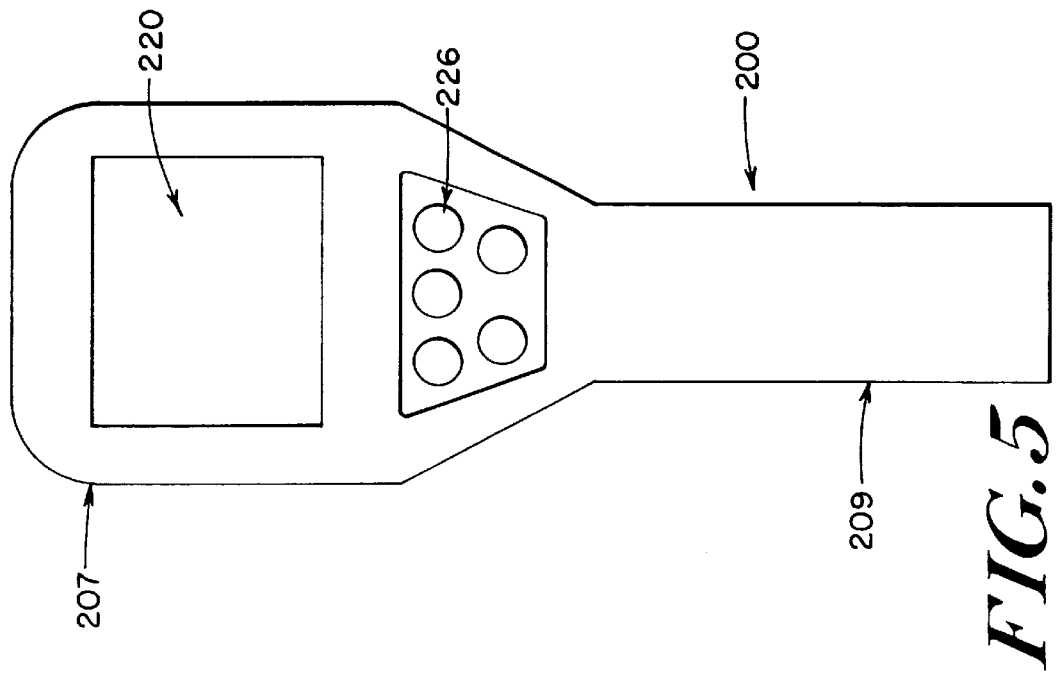
FIG. 5 is a rear elevation view of the otoscope of FIG. 3.
Figure 4:
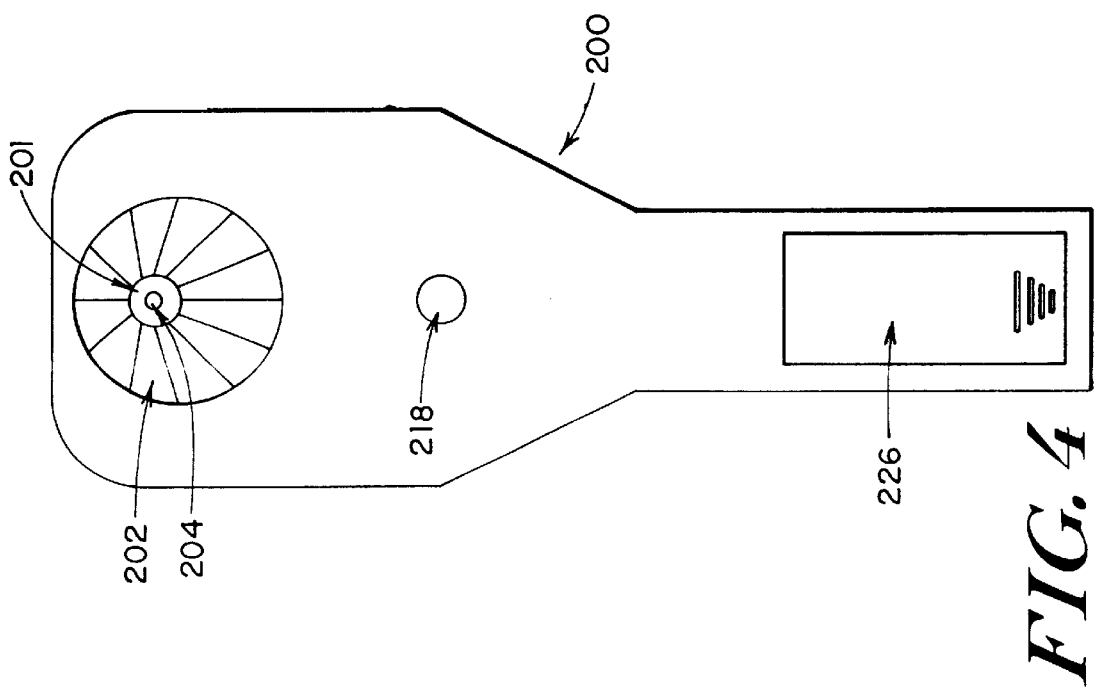
FIG. 4 is a front elevation view of the otoscope of FIG. 3.

FIGS. 2–5 illustrate a data collection device 200, implemented as a portable otoscope, according to the present invention. FIG. 2 is a block diagram overview of device 200, and FIGS. 3–5 illustrate the device in more detail. Broadly speaking, device 200 comprises a measurement apparatus for collecting diagnostic and/or image data (the speculum and camera); a memory and processor for storing and processing the collected data; a user interface to permit user interaction with device 200; and a communication port for exchange of data.

Device 200 is used by an appropriate party, typically a patient, to collect diagnostic and/or image data for later examination. Hence, a patient can collect data at a leisurely pace and in familiar, comfortable surroundings. In the embodiment illustrated and described herein, device 200 is implemented as a handheld otoscope with a self-contained digital camera. Device 200, however, could be embodied in any data collection device capable of modification for operation within a subject environment as taught herein.

Otoscope 200 comprises a head portion 207 and an elongated grip portion 209. It includes a speculum 202, a lens system 204, a digital camera element 206, a processor 208 and memory 210, a user interface 212, and a communication port 214. Otoscope 200 is used by a patient to perform a self-examination of an ear canal. The patient, at his or her own pace, may perform the examination at a remote location such as the patient's home.

User interface 212 may serve a variety of functions, depending on the particular implementation of device 200. Preferably, interface 212 comprises a display or viewing screen 220 for displaying captured images and data, as well as control or input buttons or dials 216, 218. Display screen 220 is integral to otoscope 200 and forms a part of user interface 212. It may be implemented as a liquid crystal display (LCD) or as any other appropriate display means. The display screen and input buttons are conveniently positioned, as shown in FIGS. 3–5, to allow the user to simultaneously perform an exam, view the results, and make input selections as necessary. User interface may also comprise audio output means such as a speaker and additional visual output means such as LEDs to alert or signal the user as is necessary. User interface 212 may use a menu-driven control system to facilitate user interaction. A microphone may also be provided for capture of voice records to be appended to the collected data. Depending on the type of device involved and its complexity, many other types and combinations of interface features are possible.

Speculum 202 has an elongated, conical shape conducive to insertion into and examination of a patient's ear canal. This shape is well known to those of ordinary skill in the art. Moreover, speculum 202 may be constructed of a soft material and preferably has a soft, disposable outer cover (not shown). A light source 205 mounted within or adjacent speculum 202 emits light into a central bore 201 extending through speculum 202. The light emitted by light source 205 is focused by a lens assembly 204 extending through bore 201 and exits the open end of speculum 202 to illuminate the ear canal or a target area of the ear canal. Hence, light source 205 should be positioned to accurately and efficiently convey light through bore 201 and assembly 204. To this end, light source 205 may be implemented as a single piece, conical light pipe (as is shown in FIG. 3), or as a light fiber extending through speculum 202 and possibly integrated with lens assembly 204. Alternative light sources could also be used.

Light source 205 may comprise multiple and individually controlled light sources, such as light emitting diodes (LEDs) or light bulbs. The multiple light sources may emit light within the same or different frequency ranges. Where LEDs are employed, color control (i.e. red, green, blue, ultra-violet, intra-red, etc.) of the light emitted can be obtained by using light intensity modulation and/or multiple colored sources. As will be described below, the digital camera element may respond to a wide range of frequencies. Light source 205 may also employ a pulsed operation in order to control light intensity, exposure and to provide energy savings.

Lens assembly 204 extends through and is integrated into speculum 202. The physical configuration of a suitable lens assembly will be familiar to those of ordinary skill in the art, and may comprise multiple lenses and possible a light fiber assembly (see discussion above). Lens assembly 204 is preferably removable and replaceable to provide flexibility for various applications. If device 200 were modified for dental applications, for example, it may include an angled extension.

Light emitted by light source 205 exits speculum 202, strikes the target area (ear canal), and is reflected back into speculum 202. Lens assembly 204 focuses the reflected light onto an image sensor 206. In a preferred implementation, image sensor 206 is a digital camera element employing still frame camera technology. Digital camera element 206 captures and records the image in digital form. Preferably, digital camera element 206 can respond to a wide range of frequencies, facilitating its use in conjunction with a multiple frequency light source.

Suitable digital camera elements are well known to those of ordinary skill in the art and include, without limitation, CCDs and Active Pixel arrays. In one implementation, the image captured by element 206 comprises a pixel array having a minimum resolution of 100×100 pixels, a preferable resolution of 400×600 pixels and a most preferable resolution of 1000×1000 pixels. The pixels have values representing luminance and possibly color information in digital form, and may also represent frequency bands outside of the visible spectrum of light (infra-red and ultra-violet, for example).

Processor 208 and memory 210 (FIG. 2) reside on control board 222 (FIG. 3). The digital images captured and recorded by digital camera element 206 are provided to processor 208. Processor 208 is preferably capable of basic processing of multiple images per second. Such processors are commercially available and well known to those of ordinary skill in the art. Depending on the selected mode of operation (described below), the images are displayed on display screen 220 and/or locally stored in memory 210. Memory 210 may be implemented as a RAM or any other appropriate electronic storage means.

Otoscope 200 has several modes of operation. In one mode of operation, referred to as, a still frame is captured, updated and displayed on screen 220 multiple times per second to allow the user to target the desired object or feature. Preferably, the still frame is updated in the range of 15 to 30 times per second. Upon pressing an appropriate control button 216 or 218, the user captures the currently displayed image. The user may then elect either to save the image to memory 210 or to dispose of the image.

In an alternate mode of operation, processor 208 captures multiple images and automatically selects the best image. In this mode, which the user enters by pressing an appropriate button or making an appropriate menu selection, multiple frames are captured and analyzed by processor 208. Processor 208 selects the best image for viewing, based on parameters such as alignment and focus, and displays the image on screen 220. Processor 208 may even target optimal images, and have control over camera functions such as zooming and panning to obtain the image. The user may elect to save the displayed optimal image to memory 210 or to dispose of the image. This mode is advantageous in that it solves the problem encountered by doctors and care practitioners of requiring a patient to hold still during an ear exam. Since digital camera element 206 can capture 15–30 high quality digital images per second, the impact of patient movement on image quality is minimized. Moreover, the practitioner can then carefully analyze the high quality image at his leisure without access to the patient.

In other modes of operation, the user may select frames previously stored in memory 210 for viewing. The user may also elect to delete a single stored frame or all stored frames. Finally, as will be explained in more detail below, the user may elect to export stored images to a remote site such as a base station, host PC or website.

Processor 208 preferably employs pattern matching and image analysis techniques to automatically identify suitable images from a series of images captured over a timeframe as otoscope 200 is moved around within the patient's ear. An image is considered suitable when a majority of prescribed image landmarks or characteristics are matched, indicating the presence of an eardrum, for example. Hence, processor 208 may employ image analysis to determine surface shapes, such as concavity, convexity and so on. When an image is recognized as optimal, the user may be audibly or visually alerted. Pattern matching methodologies that may be used include, without limitation, template-based matching, neural network systems and vector analysis.

In addition to the methodologies described above, pneumatic measurements may be taken to determine an object's movement. An air path may be provided to permit pneumatic operation in conjunction with the image capturing process. Hence, a series of images can be captured for manual review or automated analysis and the target object's movement in response to a blast of air can be determined. Visible, infrared and/or ultraviolet illumination, sensing and processing may also assist in obtaining data such as temperature measurements, fluid identification and enhanced image features.

Figure 6:
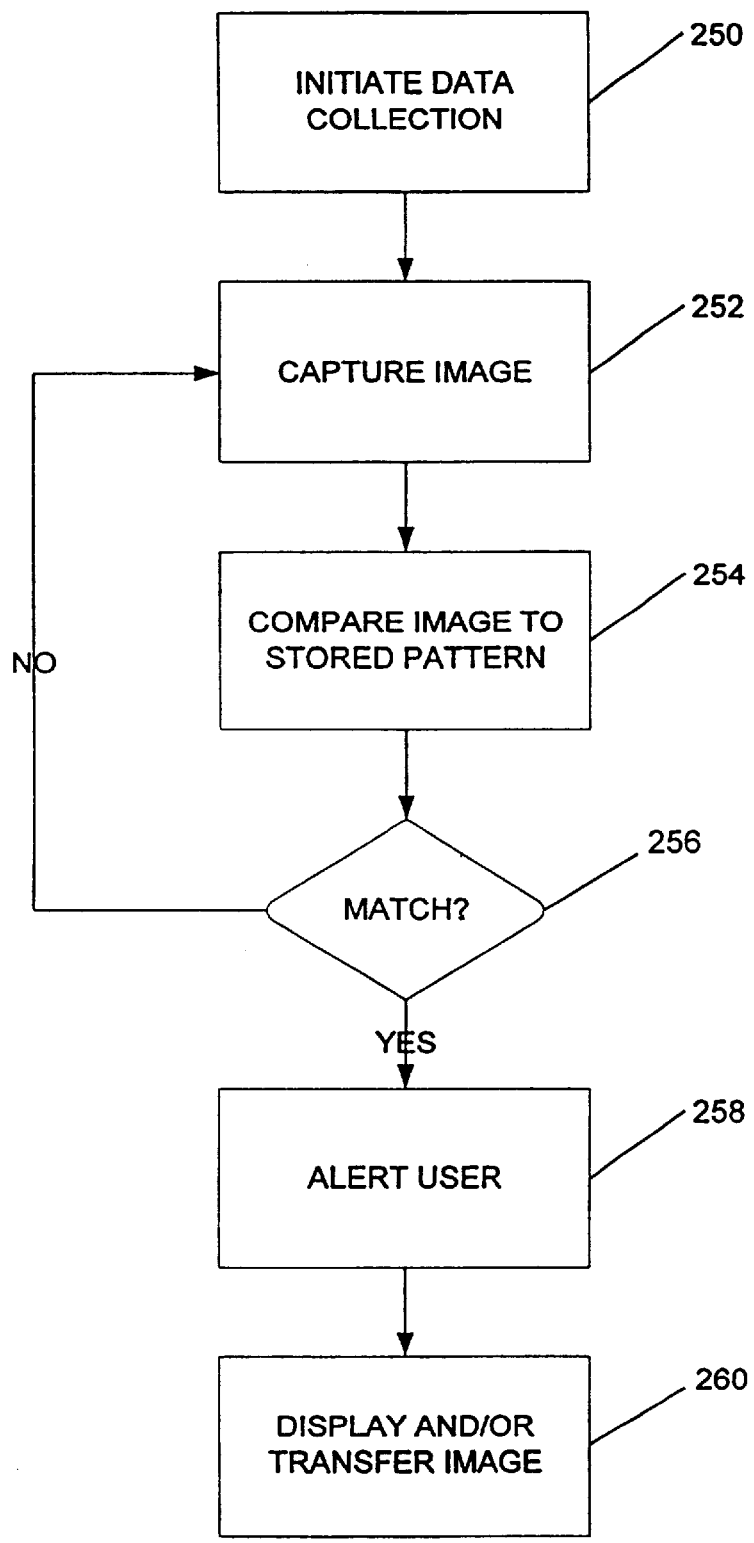
FIG. 6 is a flowchart illustrating method steps for pattern matching and image analysis according to the present invention.

One implementation of a process for pattern matching and image analysis is depicted in FIG. 6. In step 250, data collection with device 200 is initiated. Typically, this will occur when the user presses an appropriate button 216, 218 on device 200 or makes an appropriate menu selection. In step 252, digital camera element 206 captures an image. The captured image is compared with patterns or templates stored in memory 210 in step 254. At decision node 256, if the image is not a good match for an eardrum, the method returns to step 252 and captures additional images. If the image is a good match, at step 258, the user is alerted. The alert may be in the form of a beep, a flashing LED, or any other prominent user alert. The image may then be viewed on display 220 and/or transferred to an external device (step 260).

In one implementation, the images or patterns used by processor 208 for pattern matching are pre-recorded and stored on an external server or web page. The user may obtain the images by connecting to the Internet and manually downloading the appropriate images via communications port 214. Alternatively, when device 200 is connected to base station 300, the system may automatically upload the appropriate images. This method is advantageous in that the user is not required to have particular knowledge regarding the appropriate images.

Figure 7:
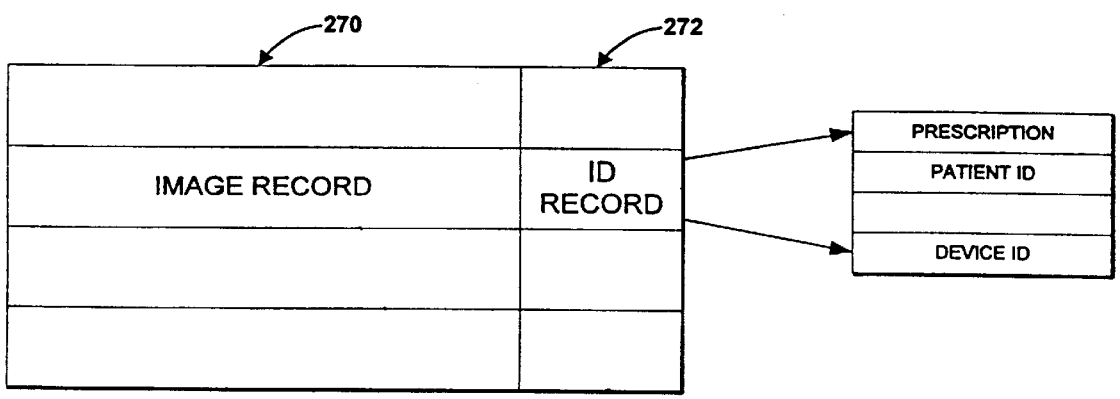
FIG. 7 is a diagram of a format for storing image and ID records according to the present invention.

As described above, the captured images and/or data are stored as records in memory 210. One possible format for storing image records 270 is depicted in FIG. 7. In addition to images, additional data such as recorded weights from a scale, heart monitor readings, and so on may be stored in records 270. Other information such as a patient ID, device ID, prescription ID and information, etc. may be appended to image records 270. This other information is stored in the form of an identification record 272 appended to or associated with each image record 270. Hence, memory 210 contains a set of image records 270 associated with a set of ID records 272. Once stored in this manner, the image and ID records may be retrieved, transmitted and/or archived at any time convenient to the patient and/or doctor. This is especially significant in medical settings, as the need for many office visits is eliminated. Moreover, ID records 272 permit efficient tracking of the patient's identity, the device used, the prescribing party and prescription, and so on.

Alternatively, identifying information such as names, numbers or bar codes, identifying the patient and the particular image, can be overlaid onto the image record and imbedded in a digital file. This reduces the need for an appended ID record and further simplifies record keeping.

Device 200 also includes a communications port 214 (FIG. 2). Communications port 214 may receive information from an external device and may transmit collected images and data to an external device for analysis and storage at a remote location. Typically, communications port 214 comprises a standard short-range interface and software protocol for communication with base unit 300. Suitable short-range data communications including direct cable, contact connectors, infrared wireless, RF wireless, and so on. In the illustrated embodiment (FIG. 3), communications port 214 takes the form of external electrical connectors. The connectors interface to and permit communication with a base unit 300, which will be described below. Alternatively, wired or wireless connections directly to an external website, server or host PC may be provided.

Finally, device 200 includes a power source 224 (accessed by a door 226) for providing power to all components within device 200. Power source 224 is typically implemented as a rechargeable battery. Where a battery is utilized, electrical connectors 214 may also be used in conjunction with base unit 300 to recharge the battery.

Figure 8:
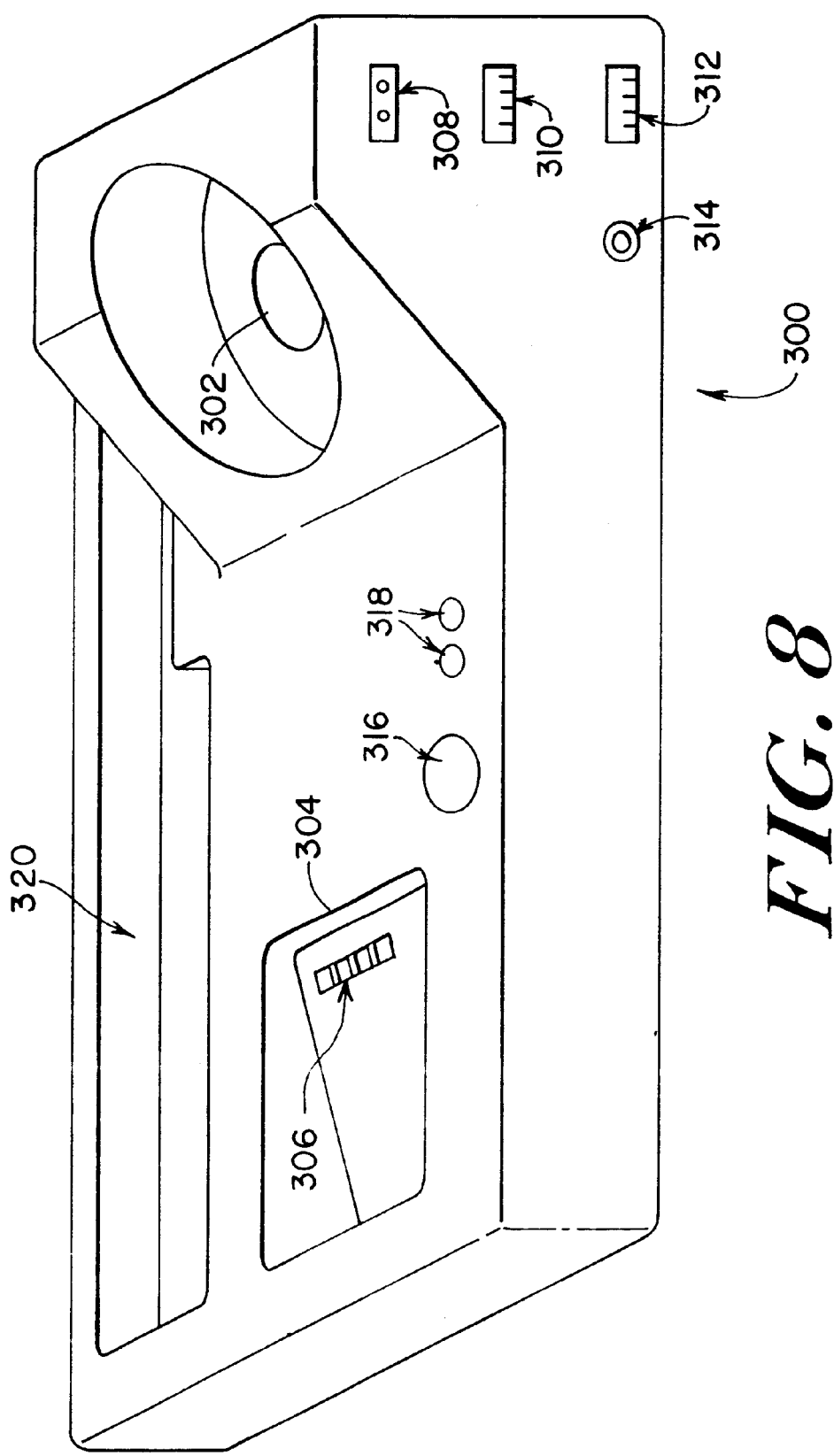
FIG. 8 is a perspective view of a base unit according to the present invention.

A base unit 300 for use with device 200 is depicted in FIG. 8. Base unit 300 comprises cradles 302 and 304 for receiving and holding, respectively, the head and grip portions 207 and 209 of otoscope 200 when it is not in use. Grip cradle portion 304 includes electrical contacts 306 that contact electrical contacts 214 of otoscope 200 when placed in base unit 300. Contacts 306 may be used to recharge otoscope battery 224, as well as to exchange information with otoscope 200. Alternatively, base unit 300 could have an infrared transceiver or other appropriate communications interface for short-range communication with otoscope 200.

Preferably, base unit 300 comprises additional universal communications ports to permit a wide range of communications with external devices, particularly with devices of the types used in healthcare settings. An infrared or wireless transceiver 308 may be provided to permit communications with an external server, computer, website or with device 200. A computer jack or interface 310 may be provided for wired communication with an external host PC or server. Telephone jack or interface 312 may be provided to permit connection to the Internet or an external telephone. In this regard, base unit 300 may comprise an integrated modem incorporating Internet protocols that is connected to interface 312. Power jack or interface 314 permits connection to an appropriate power source.

Base unit 300 also comprises a user interface. The user interface may have some or all of the features as described with reference to device 300. In the illustrated embodiment, a "send" button 316 is provided to initiate transmission of collected data to an external device, and LED indicators 318 are provided for displaying status and/or alerting or signaling the user. A storage compartment 320 facilitates physical storage of components and accessories such as speculum covers and batteries.

Though not illustrated, base unit 300 may also comprise a local processor and memory for storage and processing of image data received from otoscope 200 and authorization or instruction data received from an external device or computer.

Once images and data have been collected with device 200, device 200 may be placed in base station 300. Utilizing communications port 214, image records may be downloaded to from device 200 to base station 300 for later export to an external website, server or host PC. In the illustrated embodiment, the downloading would occur via the contacting electrical connectors. At the prompt of the user, the image records would be transmitted to an external website, server or host computer via the appropriate communications port 308, 310 or 312. The data may be encoded to ensure secure transmission. Alternatively, the image records may be transmitted directly to an external storage site via base unit 300 without intervening storage in base unit 300. Additionally, images for pattern matching and recognition may be selected and imported from an external device to base unit 300 via the appropriate communications port 308–312, and from base unit 300 to device 200 via communications port 214.

In one implementation within a system such as system 100 of FIG. 1, an appropriate authorization or prescription from server 110 is required for data collection and transmission with device 200. In this implementation, the patient first connects base unit 300 as is appropriate. This may include, for example, plugging a power line and a telephone line into jacks 310, 312. Next, device 200 is appropriately connected to base unit 300, and the user makes an appropriate selection to initiate communication with server 110. Base unit 300 then communicates with the server 110 via communications medium 140 (as indicated by line 132 of FIG. 1). The communications could, for example, involve sending a device ID. Having received the device ID number, server 110 verifies that the device has been registered, retrieves any pending prescriptions 112 . . . 114, and passes the prescriptions onto base unit 300 via communications medium 140 (line 120).

Base unit 300 transfers the prescription instructions to device 200, which can then collect the required images and/or data. The images and data are collected, processed and stored in device 200 as described above. The collected images and/or data may be transferred from device 200 to base unit 300 by appropriate user action or, with direct contacts, by placing the device in the base unit. When directed, either by the system or the user, base unit 300 transfers the data to server 110 via an appropriate communications port.

Various embodiments of the present invention have been illustrated and described herein. It should be understood, however, that these embodiments are presented by way of example only, and not limitation. Thus, the breadth and scope of the present invention is not limited by the embodiments described herein, but is defined by the following claims and their equivalents.

What is claimed is:

1. A remote data collection device in communication with a central server, the data collection device comprising:
   a digital camera for capturing diagnostic images and for responding to a wide range of frequencies;
   a processor for processing the captured images;
   a memory for storing the captured images;
   a communications port for transmitting the captured images to the central server and for receiving instructions from the central server; and
   a user interface to facilitate use of the data collection device by a remote party,
   wherein the device is a portable otoscope having a speculum and a controllable light source having individually controllable light sources that emit light in distinct frequency ranges for illuminating a target area of an ear canal and providing reflected images to the digital camera.

2. A device in communication with a central server as claimed in claim 1, wherein the light source comprises a conical light pipe.

3. A device in communication with a central server as claimed in claim 1, wherein the light source comprises light fibers extending through the speculum.

4. A device in communication with a central server as claimed in claim 1, and further comprising a lens assembly disposed within the speculum for focusing light on the target area and for focusing the reflected light onto the image sensor.

5. A device in communication with a central server as claimed in claim 1, wherein the processor performs pattern matching by comparing images obtained by the digital camera element with prerecorded eardrum images.

6. A device in communication with a central server as claimed in claim 1, wherein the communications port comprises electrical contacts configured for contact with mating contacts of an external device.

7. A device in communication with a central server as claimed in claim 6, wherein the external device is a base unit configured to receive and communicate with the device, and wherein the base unit transmits images from the data collection device to the central server, and transmits instructions from the central server to the data collection device.

8. A device in communication with a central server as claimed in claim 1, wherein the communications port comprises an infrared or wireless communications interface.

9. A device in communication with a central server as claimed in claim 1, wherein the user interface comprises buttons or keys for user input and a display screen for displaying images or collected data.

10. A device in communication with a central server as claimed in claim 9, wherein the user interface further comprises audio output and input means, and LEDs for visual output.

11. A system for remote data collection comprising:
   a remote, portable otoscope comprising a controllable light source having individually controllable light sources that emit light in distinct frequency ranges for illuminating a target area of an ear canal and generating reflected images, a digital camera element for capturing the reflected images and for responding to a wide range of frequencies, a processor for processing the reflected images, a memory for storing the processed images, and a first communications port for transmitting the processed images and receiving data from an external source;
   a base unit having a second communications port for receiving images from the otoscope and for transmitting instructions to the otoscope; and
   a central server in communication with the base unit for receiving images from the base unit and transmitting instructions to the base unit, and for receiving data collection instructions from an authorized, prescribing party.

* * * * *